(12) United States Patent
Cokonaj

(10) Patent No.: US 10,481,130 B2
(45) Date of Patent: Nov. 19, 2019

(54) AIRCRAFT HEALTH AND USAGE MONITORING SYSTEM AND TRIGGERING METHOD

(71) Applicant: Safran Landing Systems UK Limited, Gloucester (GB)

(72) Inventor: Valerijan Cokonaj, Gloucester (GB)

(73) Assignee: SAFRAN LANDING SYSTEMS UK LIMITED, Gloucester (GB)

( * ) Notice: Subject to any disclaimer, the term of this patent is extended or adjusted under 35 U.S.C. 154(b) by 177 days.

(21) Appl. No.: 15/290,633

(22) Filed: Oct. 11, 2016

(65) Prior Publication Data
US 2017/0115253 A1    Apr. 27, 2017

(30) Foreign Application Priority Data

Oct. 23, 2015 (EP) .................................. 15191345

(51) Int. Cl.
| | |
|---|---|
| *G01N 29/04* | (2006.01) |
| *G01N 29/44* | (2006.01) |
| *G07C 5/08* | (2006.01) |
| *B64D 45/00* | (2006.01) |

(52) U.S. Cl.
CPC .............. *G01N 29/04* (2013.01); *G01N 29/44* (2013.01); *G07C 5/0841* (2013.01);
(Continued)

(58) Field of Classification Search
CPC .... G01N 29/04; G01N 29/44; G01N 29/4436; G01N 2291/2694; G01N 2291/2638;
(Continued)

(56) References Cited

U.S. PATENT DOCUMENTS

| | | | |
|---|---|---|---|
| 7,322,244 B2* | 1/2008 | Kim ....................... | G01H 9/004 703/1 |
| 2003/0219191 A1* | 11/2003 | Kehlenbach ............ | G01L 1/165 385/12 |

(Continued)

FOREIGN PATENT DOCUMENTS

| | | |
|---|---|---|
| WO | 2014184521 | 11/2014 |
| WO | 2015153845 | 10/2015 |

OTHER PUBLICATIONS

"Introduction to a study of Mechanical Vibration" by G. W. Van Santen (Year: 1961).*

(Continued)

*Primary Examiner* — Natalie Huls
*Assistant Examiner* — Suman K Nath
(74) *Attorney, Agent, or Firm* — RatnerPrestia

(57) ABSTRACT

An aircraft health and usage monitoring system (HUMS) having one or more monitoring sensors arranged to be coupled to an aircraft subassembly to monitor the health of one or more parts of the subassembly and a trigger subsystem. The trigger subsystem includes a sound transducer and a processor, the processor being coupled to the sound transducer to receive and process sound signals from the sound transducer to extract sound information and being coupled to the monitoring sensors to provide control commands to the monitoring sensors. The processor is configured to provide a first control command to the monitoring sensors in response to a first criteria having been met, the first criteria including first sound information.

19 Claims, 3 Drawing Sheets

(52) U.S. Cl.
CPC ............... *B64D 2045/008* (2013.01); *G01N 2291/2694* (2013.01); *G07C 5/0808* (2013.01)

(58) Field of Classification Search
CPC ..... G01N 2291/106; G01N 2291/0289; G01N 2291/023; G01N 29/223; G01N 29/341; G01N 29/346; G01N 29/348; G01N 29/38; G01N 29/40; G01M 7/00; G01M 17/00; G06F 7/00; B64F 5/00
USPC ........ 73/584, 583, 632; 702/34, 35, 56, 189; 701/30, 31.8
See application file for complete search history.

(56) References Cited

U.S. PATENT DOCUMENTS

| | | |
|---|---|---|
| 2007/0056376 A1 | 3/2007 | King |
| 2009/0126494 A1* | 5/2009 | Karasawa ............ G01N 29/226 73/620 |
| 2009/0216398 A1 | 8/2009 | Lynch et al. |
| 2010/0121504 A1 | 5/2010 | Jones et al. |
| 2013/0211737 A1 | 8/2013 | Batcheller et al. |
| 2013/0261879 A1 | 10/2013 | Chen et al. |
| 2013/0268154 A1 | 10/2013 | Kreitmair-Steck |
| 2014/0165728 A1 | 6/2014 | Chaume et al. |

OTHER PUBLICATIONS

"Ultrasonic Testing of Materials" by Josef Krautkramer and Herbert Krautkramer (Year: 1977).*
European Search Report for EP 15191345, dated Apr. 21, 2016, 9 pages.
Communication Pursuant to Article 94(3) for European Application No. 15 191 345.6, dated Apr. 26, 2019, 8 pages.

* cited by examiner

AIRCRAFT HEALTH AND USAGE MONITORING SYSTEM AND TRIGGERING METHOD

This application claims the benefit of and priority to European Application 15191345.6, filed Oct. 23, 2015, the contents of which are incorporated herein by reference.

BACKGROUND OF THE INVENTION

It is known to provide an aircraft with a health and usage monitoring system (HUMS). A HUMS can include one or more sensors arranged to monitor parts of the aircraft to determine for example whether the parts have been subjected to mechanical loads exceeding a predetermined acceptable limit.

One type of HUMS is known in the art as an integrated vehicle health monitoring system (IVHMS), also known as an aircraft condition monitoring system (ACMS). An IVHMS is an integral part of an aircraft, which is installed at the point of aircraft manufacture.

It is also known to provide a HUMS upgrade which can be retrofitted to an in-service aircraft by interfacing the HUMS with the aircraft IVHMS and/or avionics system to receive trigger systems from the IVHMS and/or avionics system.

The present inventor has identified that HUMS can be improved in terms of one or more of the following aspects:
complexity;
weight;
degree of interference with aircraft systems; and
suitability for retrofitting to in-service aircraft.

SUMMARY OF THE INVENTION

According to a first aspect of the present invention there is provided an aircraft health and usage monitoring system (HUMS) comprising:
one or more monitoring sensors arranged to be coupled to an aircraft subassembly to monitor the health of one or more parts of the subassembly; and
a trigger subsystem comprising:
a sound transducer; and
a processor, the processor being coupled to the sound transducer to extract sound information from sound signals generated by the sound transducer and being coupled to the monitoring sensors to provide control commands to the monitoring sensors, the processor being configured to:
provide a first control command to the monitoring sensors in response to a first criteria having been met, the first criteria comprising registering first sound information.

Thus, the HUMS according to the first aspect of the invention enables the monitoring sensors to be controlled, for example activated and deactivated, in response to sounds detected by the sound transducer of the trigger subsystem. This enables the health and usage monitoring functionality of the HUMS to be controlled by operation of remote sound generating components or systems of the aircraft, without incurring the weight that would be associated with a wired connection to the remote sound generating components or systems and without incurring the potential electromagnetic interference or line of sight requirements that could result from a wireless electromagnetic or free space optics communications link with the remote sound generating components. The HUMS can therefore be relatively simple and light weight to implement. The sound based trigger subsystem also enables the HUMS to be a stand-alone system that can be retrofitted to in-service aircraft without requiring a data connection to be made to the aircraft's IVHMS and/or avionics system.

The processor can be arranged to provide a second control command to the monitoring sensors in response to a second criteria having been met, the second criteria comprising registering second information which is distinct from the first sound information. Thus, a first sound can for example activate the monitoring sensors and a second sound can for example deactivate the monitoring sensors.

The processor can be arranged in wired communication with the sound transducer to receive the sound signal from the sound transducer and arranged in wired communication with the monitoring sensors. This can reduce the likelihood of the HUMS causing electromagnetic interference with electronic aircraft systems when the HUMS is active during flight and landing operations.

The sound transducer can be arranged to be mounted on the aircraft subassembly and preferably is located adjacent to the processor. This can limit the amount of wire, and therefore weight, required to couple the sound transducer to the processor.

The sound transducer can comprise one or more of: a microphone, hydrophone, or any other transducer arranged to detect sound waves and convert the sound waves into electrical signals.

The first command can be an activation command. The activation command can cause the monitoring sensors to start monitoring the condition of the subassembly for a finite time duration, or preferably until a deactivation command is received.

The second command can be a deactivation command. The deactivation command can cause the monitoring sensors to stop monitoring the condition of the subassembly for a finite time duration, or preferably until an activation command is received.

The first sound information can comprise a sound exceeding a first threshold. The second sound information can comprise a sound below a second threshold. Alternatively or in addition, the first and second sound information can each comprise a sound signature or frequency spectra corresponding to the sound of one or more of the following aircraft events: landing gear bay door(s) opening or closing; landing gear up-lock or down-lock engaging; aircraft touchdown; aircraft taxiing; aircraft coming to rest; aircraft engines on or off; towing vehicle manoeuvring; aircraft take-off; landing gear retracted.

The trigger subsystem can further comprise one or more non-sound based transducers arranged to be mounted on the subassembly for monitoring one or more properties of the subassembly, the processor being communicatively coupled to, preferably in wired connection with, the one or more non-sound based transducers to receive input signals from them. For example, the aircraft assembly can be provided with one or more of: a proximity switch arranged to detect that a first part of the assembly has moved to a predetermined location relative to a second part of the assembly, a pressure sensor, a shock absorber travel sensor or a deflection sensor.

The first and second criteria can each further comprise receiving an input signal from the one or more of the non-sound based transducers in addition to the sound information. Thus, the processor can be configured to provide commands to the monitoring sensors in response to receiving sound information in combination with non-sound based input signal(s), which can improve the likelihood of the HUMS being activated and deactivated at the correct times. This can be advantageous when the command is to activate a wireless data readout function, which might not be desirable while the aircraft is flying, or during take-off and landing.

The HUMS can further comprise a wireless data readout device configured to provide wireless readout of data captured by the monitoring sensors during an active period. The processor can be configured to provide a readout safety command in response to a third criteria having been met, the third criteria comprising registering third sound information. The third sound information can comprise a sound below a second threshold. Alternatively or in addition, the third sound information can comprise a sound signature corresponding to the sound of one or more of the following aircraft events: aircraft coming to rest; aircraft engines off; parking brakes activated; passenger or baggage door opened. The readout safety command can provide an indication that it is safe for data readout to occur.

Data readout can be effected in any known way; for example, a maintenance engineer can connect a computing device to the HUMS via a known communications interface such as USB.

In accordance with a second aspect of the invention, there is provided an aircraft subassembly including or fitted with a HUMS according to the first aspect.

The aircraft subassembly can comprise a landing gear assembly.

In accordance with a third aspect of the invention, there is provided an aircraft including one or more subassemblies according to the second aspect.

In accordance with fourth aspect of the invention, there is provided a method of triggering monitoring sensors of an aircraft HUMS, the method comprising the steps of:
  detecting at a sound transducer a noise made by a part of an aircraft so as to generate a sound signal representative of the noise;
  transmitting the sound signal to a processor;
  at the processor, analysing the sound signal to obtain sound information from the sound signal; and
  providing a first control command to the monitoring sensors in response to a first criteria having been met, the first criteria comprising registering first sound information.

The method can comprise providing a second control command to the monitoring sensors in response to a second criteria having been met, the second criteria comprising registering second sound information.

The method can comprise a step of providing non-sound based input signal(s) to the processor and whereby the first and/or second criteria can comprise registering sound information in combination with one or more non-sound based input signals.

These and other aspects of the present invention will become apparent from, and clarified with reference to, the embodiments described herein.

BRIEF DESCRIPTION OF THE DRAWINGS

Embodiments of the present invention will now be described, by way of example only, with reference to the accompanying drawings, in which.

DESCRIPTION OF EMBODIMENTS OF THE INVENTION

Figure 1:
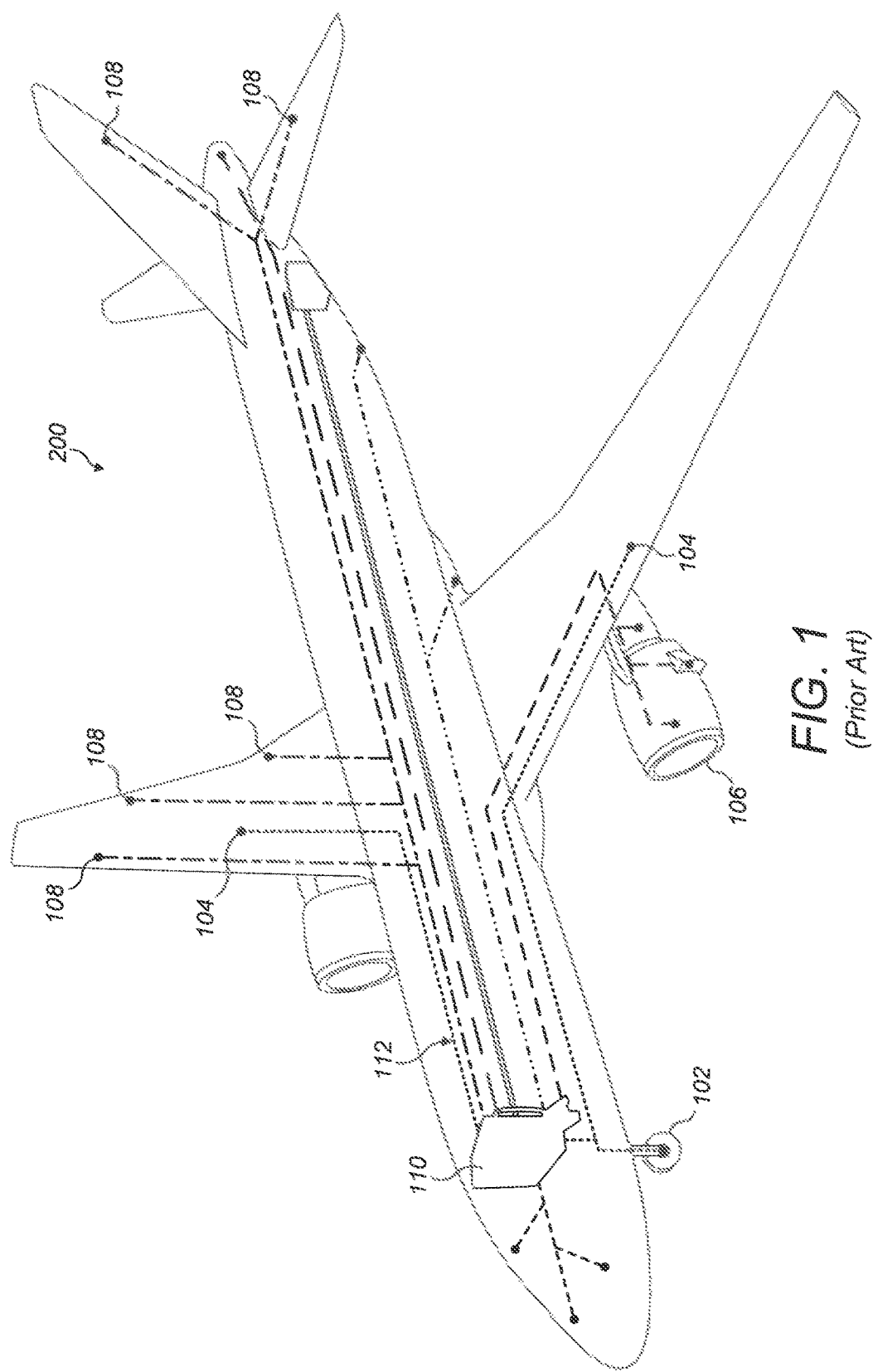
FIG. 1 is a diagram of an aircraft.

FIG. 1 is a diagram of an aircraft 200. The aircraft 200 includes subassemblies such as a nose landing gear 102, main landing gear 104, engines 106 and flaps 108. Other aircraft subassemblies will be apparent to the skilled person. A subassembly can be a group of interconnected parts which are arranged to be fitted to the aircraft as a unit.

The aircraft 200 includes a known electronic avionics system and/or integrated vehicle health monitoring system (IVHMS) 110 that is in wired communication 112 with various aircraft sensors, including sensors fitted to the subassemblies. For example, the avionics system/IVHMS 110 is in wired communication with a proximity sensor on the main landing gear 104 which provides a weight on wheels or weight off wheels signal to the avionics system 110.

Figure 2:
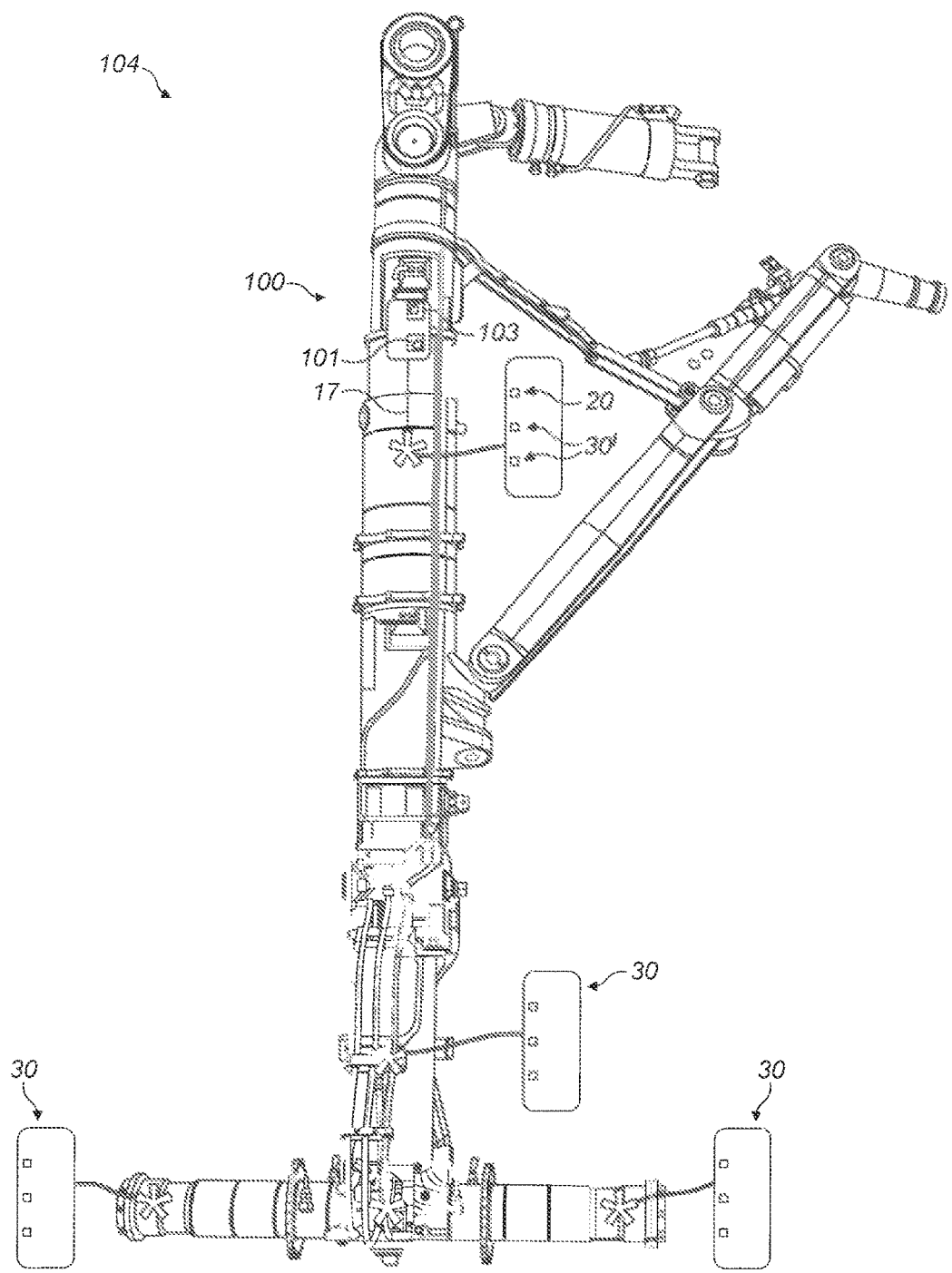
FIG. 2 is a diagram of an aircraft subassembly including a HUMS according to an embodiment of the invention.

FIG. 2 is a diagram of an aircraft subassembly 104 including a HUMS 100 according to an embodiment of the invention. The subassembly 104 in this embodiment is a main landing gear assembly 104, but in other embodiments the HUMS 100 can be fitted to other aircraft subassemblies.

The HUMS 100 is preferably restricted to the subassembly 104 in that it does not require wired or wireless electromagnetic power or data links to components of the aircraft 200 which are not part of the subassembly 104 in order to perform health and usage monitoring of components of the subassembly 104 while the aircraft 200 is operational. Thus, the HUMS 100 is not communicatively coupled or otherwise linked to the aircraft avionics system/IVHMS 110. The HUMS 100 can be coupled to aircraft systems such as the power system during non-operational phases in order to recharge batteries for example.

Figure 3:
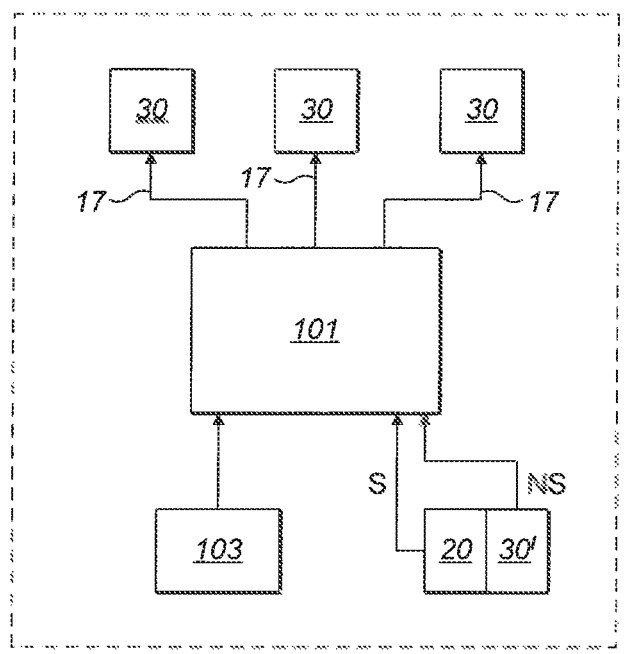
FIG. 3 is a system diagram of the HUMS of FIG. 2.

Referring additionally to FIG. 3, the HUMS 100 includes a processor 101 coupled to a plurality of monitoring sensors 30 via wired connections 17. The processor 101 can comprise a microcontroller, application specific integrated circuit (ASIC), field programmable gate array (FPGA), or other suitable computing device.

The processor 101 is configured to provide control commands such as activation and deactivation commands the monitoring sensors 30 to activate them and deactivate them respectively. The processor 101 can be further configured to provide a sleep command to the monitoring sensors 30, where they continue to be powered in readiness for activation but do not monitor. While a plurality of monitoring sensors 30 are shown, in other embodiments the HUMS can include one or more monitoring sensors 30.

The monitoring sensors 30 can comprise known monitoring sensors for monitoring assembly applications such as: shock absorber servicing condition; abnormal events; overloading detection; and towing monitoring. As will be appreciated, if the subassembly is not a landing gear assembly, different conditions may be monitored. For example, the aircraft assembly can be provided with one or more of a limit switch or proximity sensor arranged to detect a first part of the assembly having moved to a predetermined location relative to a second part of the assembly, a pressure sensor, a deflection sensor and the like.

The processor 101 is arranged in wired communication with a sound transducer 20 such as a microphone, hydrophone, or any other sound transducer arranged to detect sound waves and convert the sound waves into electrical signals. It is preferred that the sound transducer 20 is mounted on the subassembly, preferably adjacent to the processor 101 so as to limit the length of the communications link, such as a wire, between them.

The processor 101 and sound transducer 20 together define a trigger subsystem for controlling the operational state of the monitoring sensors 30. The processor 101 is configured to send control commands to the monitoring sensors 30 in response to registering sound information from the sound signal S generated by the sound transducer 20. The processor 101 can control the monitoring sensors 30 directly, or alternatively indirectly via a central HUMS control processor (not shown).

The processor 101 is configured to provide an activation control command to the monitoring sensors 30 in response to a first criteria having been met, which can comprise registering first sound information from the sound signal S generated by the sound transducer 20. The activation command can cause the monitoring sensors 30 to start monitoring or measuring the condition of the assembly 104 for a finite time duration or preferably until a deactivation command is received. Additionally, the processor 101 is configured to provide a deactivation control command to the monitoring sensors 30 in response to a second criteria having been met, which can comprise registering second sound information from the signal S generated by the sound transducer 20. The deactivation command can cause the monitoring sensors to stop monitoring or measuring the condition of the assembly 104 for a finite time duration or preferably until an activation command is received.

The processor 101 can extract receipt of sound information from the signal S provided by the sound transducer 20 using various known digital signal processing techniques; for example, noise level comparison, frequency spectra analysis/comparison, analysis of time delays in sound signals, analysis/comparison in frequency shifts of frequency spectra, comparison of overall noise levels, comparison of noise/sound signatures in time domain, comparison of noise/sound signatures in frequency domain, and the like. Known sound filtering techniques may also be employed. In one example, the processor can trigger a sensor control command upon an upper or lower sound level threshold being met. Alternatively or in addition, the sound information can each comprise a sound signature or frequency spectra corresponding to a sound template of one or more of the following aircraft events: landing gear bay door(s) opening or closing; landing gear up-lock or down-lock engaging; aircraft touchdown; aircraft taxiing; aircraft coming to rest; aircraft engines on or off; towing vehicle manoeuvring; aircraft take-off; landing gear. Various suitable sound processing techniques will be apparent to the skilled person for implementing the invention in view of the present disclosure. For example, the processor 101 can store a library of expected sound signature or frequency spectra templates which, when detected in the feed from the sound transducer, act as a trigger for the HUMS 100. It should be noted that the processor 101 can comprise a plurality of processors; for example, in some embodiments the sound signal S can be processed to extract sound information by a second processor (not shown) such that the information signal is provided to the processor 101 for trigger command generation. In either event, the processor 101 triggers control commands upon registering sound information.

The processor 101 and/or monitoring sensors 30 can be provided with associated memory for storing health and usage data that is captured while the monitoring sensors 30 are active. Health and usage data can be read out in various ways. It is however preferred that the HUMS further comprises a data readout device 103 configured to provide readout of health and usage data captured by the monitoring sensors 30 during the active period. The processor 101 can be configured to provide a readout safety command in response to a third criteria having been met which can comprise registering third sound information from the sound signal S. The third sound information can comprise a lower sound level threshold being met. Alternatively or in addition, the third sound information can comprise a sound signature corresponding to the sound of one or more of the following aircraft events: aircraft coming to rest; aircraft engines off; parking brakes activated; passenger or baggage door opened.

In preferred embodiments the trigger subsystem can include one or more non-sound based input transducers 30' arranged to be coupled to the subassembly for monitoring one or more properties of the subassembly. The processor 101 is arranged in wired communication with the non-sound based input transducers 30' to receive non-sound based input signals NS from them. The processor 101 is configured to command the monitoring sensors 30 and, where provided, the readout module 103 based on sensor data received from one or more of the non-sound based input NS transducers in addition to sound information. Thus, the first, second and/or third criteria can additionally require non-sound based input signal(s) to have been received along with the extracted sound information. Embodiments of the invention in which the processor is configured to provide commands to elements of the HUMS in response to registering sound information in combination with non-sound based input signal(s) can improve the likelihood of HUMS functionality being activated and deactivated at the correct times.

The non-sound based input transducers 30' can be the same type of sensors or similar to the monitoring transducers. The non-sound based input transducers 30' can be one or more of the monitoring transducers 30.

In some embodiments, the sound based trigger signal can be transmitted by wired connection to one or more further HUMS devices provided on the subassembly which do not include a sound based trigger system in order to trigger operation of the further HUMS devices.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parenthesis shall not be construed as limiting the claims. The word "comprising" does not exclude the presence of elements or steps other than those listed in any claim or the specification as a whole. The singular reference of an element does not exclude the plural reference of such elements and vice-versa. Parts of the invention may be implemented by means of hardware comprising several distinct elements. In a device claim enumerating several parts, several of these parts may be embodied by one and the same item of hardware or by a suitably programmed computer. The mere fact that certain measures are recited in mutually different dependent claims does not indicate that a combination of these measures cannot be used to advantage.

The invention claimed is:

1. An aircraft health and usage monitoring system (HUMS) comprising:
   one or more monitoring sensors arranged to be coupled to an aircraft subassembly to monitor the health of one or more parts of the subassembly; and
   a trigger subsystem comprising:
      a sound transducer arranged to capture sounds propagating through a fluid medium distinct from the aircraft subassembly; and a processor, the processor being coupled to the sound transducer to extract sound information from sound signals generated by the sound transducer and being coupled to the monitoring sensors to provide control commands to the monitoring sensors, the processor being configured to:
provide a first control command to the monitoring sensors in response to a first criteria having been met, the first criteria comprising registering first sound information;
wherein the first control command is an activation command which causes the monitoring sensors to activate from a completely non-operational state to start monitoring the condition of the subassembly; and
wherein the first sound information comprises a sound signature or frequency spectra of a first one of the following aircraft events: landing gear bay door(s) opening or closing; landing gear up-lock or down-lock engaging; aircraft touchdown; aircraft taxiing; aircraft coming to rest; aircraft engines on or off; towing vehicle maneuvering; aircraft take-off; and landing gear retracted.

2. The HUMS according to claim 1, wherein the processor is arranged to provide a second control command to the monitoring sensors in response to a second criteria having been met, the second criteria comprising registering second sound information which is distinct from the first sound information.

3. The HUMS according to claim 2, wherein the second command is a deactivation command which causes the monitoring sensors to stop monitoring the condition of the subassembly.

4. The HUMS according to claim 2, wherein the second sound information each comprises one or more of: a sound amplitude exceeding a positive or negative threshold value; a sound signature corresponding to one of a plurality sound signatures templates, each sound signature template being associated with the operational noise of an aircraft system; a frequency spectra corresponding to one of a plurality sound signatures templates, each frequency spectra template being associated with the operational noise of an aircraft system; and a time delay between sound signals.

5. The HUMS according to claim 2, wherein the second sound information comprises a sound signature or frequency spectra of a second one of the following aircraft events: landing gear bay door(s) opening or closing; landing gear up-lock or down-lock engaging; aircraft touchdown; aircraft taxiing; aircraft coming to rest; aircraft engines; towing vehicle maneuvering; aircraft take-off; and landing gear retracted; and wherein the first sound information is different from the second sound information.

6. The HUMS according to claim 1, wherein the processor is arranged in wired communication with the sound transducer to receive the sound signals from the sound transducer and arranged in wired communication with the monitoring sensors.

7. The HUMS according to claim 1, wherein the sound transducer is arranged to be mounted on the aircraft subassembly.

8. The HUMS according to claim 1, wherein the first sound information comprises one or more of: a sound amplitude exceeding a positive or negative threshold value; a sound signature corresponding to one of a plurality sound signatures templates, each sound signature template being associated with the operational noise of an aircraft system; a frequency spectra corresponding to one of a plurality sound signatures templates, each frequency spectra template being associated with the operational noise of an aircraft system; and a time delay between sound signals.

9. The HUMS according to claim 1, wherein the trigger subsystem further comprises one or more non-sound based transducers arranged to be mounted on the subassembly for monitoring one or more properties of the subassembly, the processor being communicatively coupled to the one or more non-sound based transducers to receive input signals from them.

10. The HUMS according to claim 9, the processor is arranged to provide a second control command to the monitoring sensors in response to a second criteria having been met, the second criteria comprising registering second sound information which is distinct from the first sound information and wherein the first and second criteria each further comprise receiving input signal(s) from the one or more of the non-sound based transducers in addition to the sound information.

11. The HUMS according to claim 1, further comprising a wireless data readout device configured to enable wireless readout of data captured by the monitoring sensors during an active period, the processor being configured to provide a data readout safety command in response to a third criteria having been met, the third criteria comprising registering third sound information.

12. The HUMS according to claim 1, wherein the sound transducer comprises a microphone configured to detect sound waves propagating through air to generate the sound signals.

13. The HUMS according to claim 1, wherein the sound transducer is not one of the monitoring sensors.

14. The HUMS according to claim 1, wherein the sound transducer is distinct from the one or more monitoring sensors such that the sound transducer is not arranged to function as a monitoring sensor.

15. An aircraft subassembly including or fitted with a usage monitoring system (HUMS), the HUMS comprising:
one or more monitoring sensors arranged to be coupled to an aircraft subassembly to monitor the health of one or more parts of the subassembly; and
a trigger subsystem comprising:
a sound transducer arranged to capture sounds propagating through a fluid medium distinct from the aircraft subassembly; and
a processor, the processor being coupled to the sound transducer to extract sound information from sound signals generated by the sound transducer and being coupled to the monitoring sensors to provide control commands to the monitoring sensors, the processor being configured to:
provide a first control command to the monitoring sensors in response to a first criteria having been met, the first criteria comprising registering first sound information;
wherein the first control command is an activation command which causes the monitoring sensors to activate from a completely non-operational state to start monitoring the condition of the subassembly; and
wherein the first sound information comprises a sound signature or frequency spectra of a first one of the following aircraft events: landing gear bay door(s) opening or closing; landing gear up-lock or down-lock engaging; aircraft touchdown; aircraft taxiing; aircraft coming to rest; aircraft engines on or off; towing vehicle maneuvering; aircraft take-off; and landing gear retracted.

16. The aircraft subassembly according to claim 15, wherein the aircraft subassembly comprises a second HUMS including a second processor and one or more second monitoring sensors arranged to be coupled to the aircraft subassembly to monitor the health of one or more parts of the subassembly, wherein the trigger subsystem of the HUMS is coupled to the second processor of the second HUMS, the second processor being coupled to the second monitoring sensors to provide control commands to the second monitoring sensors, the second processor being configured to: provide the first control command to the second monitoring sensors in response to receiving the first control command from the processor of the HUMS.

17. A method of triggering monitoring sensors of an aircraft HUMS, the HUMS comprising a sound transducer and a processor, the method comprising the steps of:
  detecting at the sound transducer a noise made by a part of an aircraft so as to generate a sound signal representative of the noise wherein the noise made by the part of the aircraft has reached the sound transducer through a fluid medium;
  transmitting the sound signal to the processor;
  at the processor, processing the sound signal to extract sound information; and
    providing a first control command to trigger the monitoring sensors in response to a first criteria having been met, the first criteria comprising registering first sound information
    wherein the first control command is an activation command which causes the monitoring sensors to activate from a completely non-operational state to start monitoring the condition of the subassembly; and
    wherein the first sound information comprises a sound signature or frequency spectra of a first one of the following aircraft events: landing gear bay door(s) opening or closing; landing gear up-lock or down-lock engaging; aircraft touchdown; aircraft taxiing; aircraft coming to rest; aircraft engines on or off; towing vehicle maneuvering; aircraft take-off; and landing gear retracted.

18. The method according to claim 17, further comprising providing a second control command to the monitoring sensors in response to a second criteria having been met, the second criteria comprising registering second information and/or providing non-sound based input signal(s) to the processor, whereby the first and/or second criteria comprises registering sound information in combination with one or more non-sound based input signals.

19. An aircraft health and usage monitoring system (HUMS) comprising:
  one or more monitoring sensors arranged to be coupled to an aircraft subassembly to monitor the health of one or more parts of the subassembly; and
  a trigger subsystem comprising:
    a sound transducer, distinct from the one or more monitoring sensors, the sound transducer being arranged to capture sounds propagating through a fluid medium distinct from the aircraft subassembly; and
    a processor, the processor being coupled to the sound transducer to extract sound information from sound signals generated by the sound transducer and being coupled to the monitoring sensors to provide control commands to the monitoring sensors, the processor being configured to:
      provide a first control command to the monitoring sensors in response to a first criteria having been met, the first criteria comprising registering first sound information;
      provide a second control command to the monitoring sensors in response to a second criteria having been met, the second criteria comprising registering second sound information which is distinct from the first sound information;
      wherein the first command is an activation command which causes the monitoring sensors to activate from a completely non-operational state, and to start monitoring the condition of the subassembly;
      wherein the second command is a deactivation command which causes the monitoring sensors to stop monitoring the condition of the subassembly; and
      wherein the first sound information comprises a sound signature or frequency spectra of one or more of the following aircraft events: landing gear bay door(s) opening or closing; landing gear up-lock or down-lock engaging; aircraft touchdown; aircraft taxiing; aircraft coming to rest; aircraft engines on or off; towing vehicle maneuvering; aircraft take-off; and landing gear retracted, and
      wherein the second sound information comprises a sound signature or frequency spectra of one or more of the following aircraft events: landing gear bay door(s) opening or closing; landing gear up-lock or down-lock engaging; aircraft touchdown; aircraft taxiing; aircraft coming to rest; aircraft engines on or off; towing vehicle maneuvering; aircraft take-off; and landing gear retracted.

* * * * *